United States Patent [19]

Longhini

[11] Patent Number: 4,590,318

[45] Date of Patent: May 20, 1986

[54] METHOD FOR PRODUCING VINYL CHLORIDE

[75] Inventor: David A. Longhini, Uniontown, Ohio

[73] Assignee: PPG Industries, Inc., Pittsburgh, Pa.

[21] Appl. No.: 674,192

[22] Filed: Nov. 23, 1984

[51] Int. Cl.$^4$ .................... C07C 17/34; C07C 21/06
[52] U.S. Cl. ................................. 570/220; 570/226
[58] Field of Search ............................. 570/220, 226

[56] References Cited

U.S. PATENT DOCUMENTS 3,655,787  4/1972  Wiley ........................ 260/656 R
3,920,761  11/1975  Krome .......................... 570/226
4,324,932  4/1982  Link et al. ...................... 570/226

FOREIGN PATENT DOCUMENTS 1225210  3/1971  United Kingdom .
1384407  2/1975  United Kingdom ............. 570/226

OTHER PUBLICATIONS

McPherson, Starks, and Fryar, "Vinyl Chloride Monomer . . . What You Should Know," *Hydrocarbon Processing*, Mar. 1979, pp. 75–88.

*Primary Examiner*—Charles F. Warren
*Assistant Examiner*—John A. Sopp
*Attorney, Agent, or Firm*—George D. Morris

[57] ABSTRACT 1,2-Dichloroethane is pyrolyzed in a pyrolysis furnace to produce a stream comprising vinyl chloride and 1,2-dichloroethane. The stream is removed from the furnace and introduced to essentially unheated conduit means to establish a stream flowing in the conduit means. Pyrolysis promoter is introduced to the stream in the conduit means and sensible heat of the stream is utilized in the conduit means to pyrolyze further amounts of 1,2-dichloroethane and to increase the yield of vinyl chloride.

21 Claims, No Drawings

METHOD FOR PRODUCING VINYL CHLORIDE

It is well known that vinyl chloride can be produced by the pyrolysis of 1,2-dichloroethane, also known as ethylene dichloride. See for example, U.S. Pat. No. 3,655,787, the entire disclosure of which is incorporated by reference.

Various materials have been added in small amounts to promote the pyrolysis reaction. The promoter is added to the 1,2-dichloroethane feedstock before the feedstock is introduced to the pyrolysis furnace or it is added to the gaseous reaction mixture at one or more points within the furnace. During this reaction, the promoter is essentially consumed. Although promoters enhance the desired pyrolysis reaction, many of them also increase the amount of undesirable coke produced. This appears to be especially the case when the promoter is introduced within the furnace. Molecular chlorine, for example, when introduced within the furnace, increases coke formation.

The pyrolysis of 1,2-dichloroethane is an endothermic reaction and is favored by conditions of elevated temperature. The hydrochlorination of vinyl chloride with hydrogen chloride to produce 1,1-dichloroethane is an exothermic reaction and is favored by conditions of temperature which, although elevated when compared with ordinary ambient temperatures, are lower than those customarily employed in the pyrolysis reaction. The formation of coke is also favored at these lower temperatures.

The technique heretofore employed in the art has been to quench the effluent from the pyrolysis furnace as quickly as possible, it being thought that failure to do so would result in conversion of some of the vinyl chloride to 1,1-dichloroethane and the formation of coke. It has also been reported that if cooling is done too slowly, substantial yield losses to heavy ends and tars result; see McPherson, Starks, and Fryar, "Vinyl Chloride Monomer . . . What You Should Know," *Hydrocarbon Processing*, March, 1979, pages 75–88, at page 79. Accordingly, in practicing the prior procedure it was desired (1) that the transfer line or lines from the pyrolysis furnace to the quenching zone be as short as reasonably possible in order to minimize reduction of the stream temperature during transfer, and (2) that the quenching zone be such as to reduce the temperature as quickly as reasonably possible to at least a value where the various reactions for practical purposes ceased.

As the effluent from the furnace passes through the transfer line, some small amount of continued pyrolysis of 1,2-dichloroethane to form vinyl chloride probably does occur. Inasmuch as the reaction is endothermic and since heat is not supplied from without, any such reaction results in a commensurate reduction in the temperature of the stream. But by striving to minimize temperature reduction in the transfer line, the prior art also inherently sought to minimize pyrolysis of 1,2-dichloroethane in the transfer line.

In contradistinction to the prior art, applicant has found that the pyrolysis of 1,2-dichloroethane to form vinyl chloride should be encouraged to take place in the transfer line, notwithstanding the reduction in temperature which results. Surprisingly, the rate of coke formation in the transfer line is low, and it has been found that the rate of 1,1-dichloroethane formation is also low. In essence applicant has discovered (1) that sensible heat of the stream in the transfer line may be used to continue the pyrolysis reaction begun in the furnace, (2) that a material reduction in the temperature of the stream in the transfer line is essentially not detrimental, (3) that pyrolysis in the transfer line may, if desired, be continued until the temperature has been reduced to a value where the rate of pyrolysis is low, and (4) that pyrolysis in the transfer line may advantageously be encouraged by the addition of pyrolysis promoter to the stream in the transfer line.

Therefore, in a method for producing vinyl chloride by pyrolysis of 1,2-dichloroethane wherein: (a) 1,2-dichloroethane is pyrolyzed in a heated furnace to produce at least one stream comprising vinyl chloride and 1,2-dichloroethane, and (b) the stream is removed from the furnace and then introduced to essentially unheated conduit means to establish a stream flowing in the conduit means, the invention is the improvement comprising introducing to the stream in the conduit means a pyrolysis-promoting amount of promoter and utilizing sensible heat of the removed stream in the conduit means to pyrolyze 1,2-dichloroethane to produce vinyl chloride.

Substantially any promoter which promotes the pyrolysis reaction may be used. Often the promoter is a halogen-containing compound. Examples of promoters which may be used include molecular oxygen, molecular chlorine, molecular bromine, molecular iodine, carbon tetrachloride, carbon tetrabromide, bromotrichloromethane, dibromodichloromethane, tribromochloromethane, nitrosyl chloride, trichloroacetyl chloride, tribromoacetyl bromide, trichloroacetyl bromide, chloral, hexachloroacetone, and hexabromoacetone. Molecular chlorine is preferred. Only one promoter or a plurality of promoters may be used as desired.

A pyrolysis-promoting amount of promoter is an amount of promoter which results in an increase in the yield of vinyl chloride based on 1,2-dichloroethane, as compared with the yield of vinyl chloride produced in the absence of the promoter under otherwise substantially identical conditions. The pyrolysis-promoting amount of promoter employed may vary widely. Usually, however, the promoter is introduced to the stream at a weight rate ratio of the promoter to the stream in the range of from about 0.0001:1 to about 0.005:1. Typically, the weight rate ratio is in the range of from about 0.0005:1 to about 0.002:1. From about 0.001:1 to about 0.0015:1 is preferred.

The conduit means is usually ordinary piping used to convey the stream from the furnace to the quenching zone. One or more hold-up vessels may be included where desired. The conduit means may comprise one transfer line or a plurality of transfer lines.

In general, the retention time in the conduit means should be sufficient to achieve more than a trivial increase in vinyl chloride content before the stream is introduced to the quenching zone. In those instances where an existing transfer line does not provide the sufficient retention time for a given mass flow rate, the transfer line may be made longer, some or all of the transfer line may be replaced by a larger line, one or more hold-up vessels may be inserted, or one or more lines may be added in parallel.

The promoter may be introduced to the conduit means at one or more locations. The locations should be chosen such that there is sufficient residence time downstream to accomplish the desired pyrolysis. In most instances at least a portion of the promoter is introduced to the stream near the point where the stream removed from the furnace has been introduced to the conduit means. Ordinarily, at least a portion of the promoter is introduced to the stream within the first 20 percent of the total volume of the conduit means. In many cases at least a portion of the promoter is introduced to the stream within the first 10 percent of the total volume of the conduit means. Generally all of the promoter is introduced within the first 20 percent of the total volume of the conduit means. Preferably all of the promoter is introduced within the first 10 percent of the total volume of the conduit means. It is especially preferred that all of the promoter be introduced within the first 5 percent of the total volume of the conduit means.

Eventually, the stream leaves the conduit means. The reduction in stream temperature occurring in the conduit means may vary widely, but it is more than an inconsequental amount. Often the temperature of the stream leaving the conduit means is at least about 20 Celsius degrees less than the temperature of the stream removed from the furnace. In many cases the temperature of the stream leaving the conduit means is at least about 40 Celsius degrees less than the temperature of the stream removed from the furnace. Frequently, the temperature of the stream leaving the conduit means is at least about 60 Celsius degrees less than the temperature of the stream removed from the furnace.

In most cases the stream in the conduit means is passed from the conduit means to cooling means where the temperature of the stream is reduced to at least as low as about 180° C. In many cases the temperature of the stream is reduced in the cooling means to at least as low as about 160° C. Applicant has discovered that rapid temperature reduction in the cooling means, while preferred, is not essential.

The cooling means used may be widely varied in detail. In one embodiment, the temperature of stream passed to the cooling means may be reduced by transferring heat form the stream to coolant which is not in direct contact with the stream. Examples of cooling means of this type include double-pipe heat exchangers and shell and tube heat exchangers. In a second embodiment, the temperature of the stream passed to the cooling means may be reduced by transferring heat from the stream to coolant which is admixed with the stream. The coolant is generally cool liquid 1,2-dichloroethane or a cool liquid composition comprising 1,2-dichloroethane. Examples of cooling means that may be used for this embodiment include spray towers, packed towers, bubble cap towers, sieve tray towers and liquid pools.

It is preferred that the cooling means be quenching means of the second embodiment described above wherein the temperature of the stream is rapidly reduced by direct contact with coolant. Any of the various conventional quenching means known to the prior art may be employed. See U.S. Pat. No. 3,655,787 which describes a suitable quench system. In another quench system, cool liquid 1,2-dichloroethane or a cool liquid composition comprising 1,2-dichloroethane may be injected into a line containing the stream from the conduit means.

Substantially any furnace used for pyrolysis reactions may be employed in the invention. The most commonly used furnace, however, is a conventional tube furnace in which fuel is burned to heat tubes through which the reaction mixture passes.

The pyrolysis is conducted in the vapor phase, both within the furnace and in the conduit means. It is usually conducted continuously.

The temperature at which the pyrolysis is conducted in the furnace may vary widely, but ordinarily they are in the range of from about 350° C. to about 650° C. Preferably, the temperatures are in the range of from about 400° C. to about 550° C. These ranges of temperatures are also representative of those at which the stream comprising vinyl chloride and 1,2-dichloroethane is usually removed from the pyrolysis furnace. The removed stream is then introduced to the conduit means to establish a stream flowing in the conduit means.

Similarly the temperatures at which the pyrolysis is conducted within the conduit means are susceptible to wide variation. Generally these temperatures are in the range of from about 325° C. to about 650° C. Temperatures in the range of from about 350° C. to about 550° C. are preferred.

The pressures at which the pyrolysis is conducted, whether in the furnace or in the conduit means, may also be widely varied. While the pyrolysis may be conducted at ambient atmospheric pressure or below ambient atmospheric pressure, it is ordinarily conducted at pressures above ambient atmospheric pressure. Typically, the pressures are in the range of from about 80 to about 3500 kilopascals, gauge. Often it is in the range of from about 300 to about 2000 kilopascals, gauge. From about 700 to about 1100 kilopascals, gauge is preferred.

Likewise, the residence time of the reaction mixture in the furnace may vary widely. Generally the residence time is in the range of from about 0.1 to about 30 seconds. Often it is in the range of from about 1 to about 20 seconds. From about 3 to about 15 seconds is preferred.

The residence time of the stream in the conduit means from the first point of promoter introduction until the stream leaves the conduit means may be varied considerably. Ordinarily the residence time is in the range of from about 0.05 to about 10 seconds. In many cases it is in the range of from about 0.1 to about 5 seconds. From about 0.15 to about 2 seconds is preferred.

Following cooling, the vinyl chloride may be recovered by any of the various techniques known to the art. Fractional distillation, vaporization, and condensation are techniques which are frequently employed.

Purified vinyl chloride has a multitude of uses, but principally it is used as a monomer for producing homopolymers and interpolymers.

As used herein, "conversion" is the percentage of 1,2-dichloroethane converted to other compounds during the reaction, "selectivity" is the ratio of the moles of vinyl chloride produced to the moles of 1,2-dichloroethane converted to all products of the reaction, expressed as percent, and "yield" is the percentage of 1,2-dichloroethane converted to vinyl chloride during the reaction. "Yield" is the product of "conversion" and "selectivity" divided by one hundred.

The invention is further described in conjunction with the following examples which are to be considered illustrative rather than limiting.

EXAMPLE I

The outlet of a tube from a pyrolysis furnace where 1,2-dichloroethane was pyrolyzed to vinyl chloride, was connected to a conventional quench tower by a transfer line 10 meters in length. Provision was made for introduction of molecular chlorine into the transfer line at a point 2.4 meters downstream from the furnace outlet. Three temperature measuring devices were installed along the transfer line as follows: the first at the furnace outlet, the second 0.6 meter downstream of the point of chlorine introduction, and the third 6.1 meters downstream of the point of chlorine introduction. A sampling tee was installed very near the third temperature measuring device. In operation, a small flow of gas passed from the transfer line through the sampling tee and then through a small line to a tee where molecular nitrogen was introduced. The resulting gas mixture flowed past a septum to a vent. From time to time samples were taken through the septum using a syringe. The temperature at the first temperature measuring device was in the range of from about 454° C. to about 510° C. A normal temperature drop between the first and third temperature measuring devices was in the range of from about 28 to about 33 Celsius degrees when no chlorine was introduced to the transfer line. The total residence time in the transfer line was in the range of from about 0.15 to about 0.3 seconds.

The pressure of the stream at the furnace outlet was about 689 kilopascals, gauge. Chlorine was introduced from a cylinder which was heated using cooling water from the primary quench condenser. A pressure regulator was used to control the chlorine pressure at about 758 kilopascals, gauge. The rate of chlorine introduction was monitored by a rotameter.

The sampling procedure consisted of collecting one or more sets of 4 to 5 individual samples through the septum before and after chlorine addition. The samples were analyzed within 15 minutes after being collected. A set was considered satisfactory when the 1,2-dichloroethane conversion calculated from the individual samples were within 1.5% of each other. If a set was not satisfactory, the procedure was repeated until a satisfactory set was obtained. For a satisfactory set, the individual sample analyses were averaged before calculating a conversion or a selectivity.

Samples were collected before chlorine addition for each experiment. Immediately after the samples taken before chlorine addition were analyzed and it was determined that the set was satisfactory, chlorine was introduced to the transfer line at the point described above. During chlorine introduction, samples were not collected until the temperatures indicated by the temperature measuring devices were essentially constant.

Table 1 shows the decrease in temperature at the third temperature measuring device as a function of chlorine concentration of the stream at the point of chlorine introduction, assuming perfect mixing, viz., the chlorine addition level. More specifically, $\Delta T$ equals the temperature before chlorine introduction minus the temperature during chlorine introduction.

TABLE 1

| Chlorine Concentration, ppm | $\Delta T$, Celsius degrees |
| --- | --- |
| 0 | 0 |
| 200 | 7 |
| 400 | 11 |
| 400 | 12 |
| 500 | 25 |
| 510 | 23 |
| 670 | 27 |
| 800 | 31 |
| 1100 | 43 |
| 1200 | 44 |
| 1500 | 44 |

Table 2 shows the increase in conversion of 1,2-dichloroethane as a function of chlorine addition level.

TABLE 2

| Chlorine Concentration, ppm | Increase in Conversion, percent |
| --- | --- |
| 0 | 0 |
| 300 | 2.0 |
| 475 | 4.1 |
| 500 | 5.0 |
| 590 | 6.5 |
| 700 | 5.7 |
| 800 | 7.3 |
| 800 | 8.1 |
| 1000 | 10.2 |
| 1130 | 9.8 |
| 1260 | 10.0 |
| 1420 | 10.8 |
| 1550 | 10.2 |

The temperature at the second temperature measuring device, located 0.6 meter downstream from the point of chlorine introduction, was 16 Celsius degrees lower when the chlorine addition level was 800 parts per million, as compared to the temperature when no chlorine was introduced. This indicates that the promotion reaction occurs very rapidly Gas taken through the sample tee was bubbled through an o-tolidine solution. The o-tolidine solution was very sensitive to chlorine and would turn yellow at chlorine concentrations of one part per million. It was observed that the o-tolidine solution would turn yellow at chlorine addition levels above 800 ppm.

The vinyl chloride selectivities were greater than about 99 percent irrespective of whether or not chlorine was introduced; therefore the data show that the yield of vinyl chloride was increased due to the introduction of chlorine.

EXAMPLE II

The outlet of a tube from a pyrolysis furnace where 1,2-dichloroethane was pyrolyzed to vinyl chloride, was connected to a quench tower by a transfer line. The furnace comprised three radiant zones, each of which contained 3.35 meters of tube. A temperature measuring device was installed at the junction of the furnace tube and the transfer line. Provision was made for introduction of molecular chlorine into the transfer line a few centimeters downstream from the temperature measuring device. For a first run, the furnace outlet temperature was adjusted so that, in the absence of chlorine introduction, the conversion of 1,2-dichloroethane was 55%. For a second run, the furnace outlet temperature was adjusted so that, with the introduction of 575 parts per million of chlorine, the conversion of 1,2-dichloroethane was 55%. For a third run, the furnace outlet temperature was adjusted to approximately that of the first run, 575 parts per million of chlorine was added, and the effect on 1,2-dichloroethane conversion was noted. The date are shown in Table 3.

TABLE 3

| Run | 1 | 2 | 3 |
| --- | --- | --- | --- |
| Chlorine Concentration, ppm | 0 | 575 | 575 |
| Conversion, percent | 55 | 55 | 60 |
| Furnace Outlet Temperature, °C. | 516 | 502 | 517 |

A comparison of Run 3 with Run 1 shows that at essentially the same furnace outlet temperature, the introduction of chlorine resulted in a 9.1% increase in conversion of 1,2-dichloroethane.

A comparison of Run 2 with Run 1 shows that with chlorine addition the furnace outlet temperature was reduced 14 Celsius degrees in order to maintain a constant conversion of 1,2-dichloroethane. In order to ascertain whether the reduction in temperature was attributable to a promotion effect by the chlorine or whether it was attributable to mere dilution by the chlorine, two further runs were made to observe the effect of dilution by molecular nitrogen. The fourth run was a new baseline run. Immediately after the fourth run was completed, a fifth run was made wherein the furnace outlet temperature was adjusted so that, with the introduction of 575 parts per million of nitrogen, the conversion of 1,2-dichloroethane was the same as that of the fourth run. The data are shown in Table 4.

TABLE 4

| Run | 4 | 5 |
| --- | --- | --- |
| Nitrogen Concentration, ppm | 0 | 575 |
| Conversion, percent | 55 | 55 |
| Furnace Outlet Temperature, °C. | 521 | 519 |

It may be seen that the temperature reduction with chlorine introduction is not accounted for by dilution with nitrogen. Since the addition of chlorine allowed a large reduction in furnace outlet temperature while maintaining the same conversion and since the magnitude of the reduction is not accounted for by dilution effects, additional reaction must have been taking place outside the furnace in the transfer line.

The vinyl chloride selectivities were greater than about 98.5 percent irrespective of whether or not chlorine was introduced; therefore the data show that the yield of vinyl chloride was increased due to the introduction of chlorine.

The selectivities of 1,1-dichloroethane (viz., the ratio of the moles of 1,1-dichloroethane produced to the moles of 1,2-dichloroethane converted to all products of the reaction, expressed as percent) essentially remained in the same range with chlorine introduction as without such introduction, namely from about 0.05 percent to about 0.25 percent.

EXAMPLE III

In runs similar to that of Run 2 of Table 3, the amount of chlorine introduced was varied and the reduction in furnace outlet temperature necessary to preserve a 55% conversion of 1,2-dichloroethane was noted. The data are shown in Table 5.

TABLE 5

| Run | 6 | 7 | 8 | 9 |
| --- | --- | --- | --- | --- |
| Chlorine Concentration, ppm | 0 | 500 | 1000 | 1900 |
| Conversion, percent | 55 | 55 | 55 | 55 |
| Reduction in Furnace Outlet Temperature, Celsius degrees | 0 | 14 | 19 | 21 |

EXAMPLE IV

Using the apparatus of Example II, the effect of adding chlorine simultaneously at more than one point was studied. Approximately half of the chlorine flow introduced at an individual point was added at two points so that substantially the same quantity of chlorine was added. The first addition point was at the beginning of the third radiant section of the furnace. The second addition point was that described in Example II. The reductions in furnace outlet temperature necessary to preserve a constant conversion of 1,2-dichloroethane was noted. The data are shown in Table 6.

TABLE 6

| Run | Chlorine Concentration, ppm | | Reduction in Furnace Outlet Temperature Celsius degrees |
| --- | --- | --- | --- |
| | First Point | Second Point | |
| 10 | 0 | 0 | 0 |
| 11 | 575 | 0 | 13.7 |
| 12 | 0 | 575 | 13.7 |
| 13 | 290 | 290 | 19.2 |
| 14 | 1000 | 0 | 20.1 |
| 15 | 0 | 1000 | 18.8 |
| 16 | 500 | 500 | 29.5 |

Although the present invention has been described with reference to specific details of certain embodiments thereof, it is not intended that such details should be regarded as limitations upon the scope of the invention except insofar as they are included in the accompanying claims.

I claim:

1. In a method for producing vinyl chloride by pyrolysis of 1,2-dichloroethane wherein:
   (a) 1,2-dichloroethane is pyrolyzed in a heated furnace to produce at least one stream comprising vinyl chloride and 1,2-dichloroethane, and
   (b) said stream is removed from said furnace and then introduced to essentially unheated conduit means to establish a stream flowing in said conduit means, the improvement comprising introducing to said stream in said conduit means a pyrolysis-promoting amount of promoter and utilizing sensible heat of said removed stream in said conduit means to pyrolyze 1,2-dichloroethane to produce vinyl chloride.

2. The method of claim 1 wherein said promoter is introduced to said stream in said conduit means at a weight ratio of said promoter to said removed stream in the range of from about 0.0001:1 to about 0.005:1.

3. The method of claim 1 wherein at least a portion of said promoter is introduced to said stream in said conduit means near the point where said removed stream has been introduced to said conduit means.

4. The method of claim 1 wherein at least a portion of said promoter is introduced to said stream in said conduit means within the first 20 percent of the total volume of said conduit means.

5. The method of claim 1 wherein all of said promoter is introduced to said stream in said conduit means within the first 20 percent of the total volume of said conduit means.

6. The method of claim 1 wherein said promoter is halogen-containing promoter.

7. The method of claim 1 wherein said promoter is molecular chlorine.

8. The method of claim 1 wherein said stream flowing in said conduit means leaves said conduit means and wherein the temperature of said leaving stream is at least about 20 Celsius degrees less than the temperature of said removed stream.

9. The method of claim 1 wherein said stream flowing in said conduit means leaves said conduit means and wherein the temperature of said leaving stream is at least about 40 Celsius degrees less than the temperature of said removed stream.

10. The method of claim 1 wherein said stream flowing in said conduit means leaves said conduit means and wherein the temperature of said leaving stream is at least about 60 Celsius degrees less than the temperature of said removed stream.

11. The method of claim 1 wherein said stream in said conduit means is passed from said conduit means to cooling means where the temperature of said stream is reduced to at least as low as about 180° C.

12. The method of claim 11 wherein the temperature of said stream passed to said cooling means is reduced by transferring heat from said stream to coolant which is not in direct contact with said stream.

13. The method of claim 11 wherein the temperature of said stream passed to said cooling means is reduced by transferring heat from said stream to coolant which is admixed with said stream.

14. The method of claim 11 wherein said cooling means is quenching means wherein the temperature of said stream is rapidly reduced by direct contact with coolant.

15. In a method for producing vinyl chloride by pyrolysis of 1,2-dichloroethane wherein:
   (a) 1,2-dichloroethane is pyrolyzed at one or more temperatures in the range of from about 350° C. to about 650° C. in a heated furnace to produce at least one stream comprising vinyl chloride and 1,2-dichloroethane,
   (b) said stream is removed from said furnace at a temperature in the range of from about 350° to about 650° C. and then introduced to essentially unheated conduit means to establish a stream flowing in said conduit means, and
   (c) said stream in said conduit means is passed from said conduit means to quenching means wherein the temperature of said stream is rapidly reduced to at least as low as about 180° C. by direct contact with coolant.

the improvement comprising introducing to said stream in said conduit means, within the first 20 percent of the total volume of said conduit means, a pyrolysis-promoting amount of molecular chlorine to promote within said conduit means the pyrolysis of 1,2-dichloroethane to produce vinyl chloride.

16. The method of claim 15 wherein said molecular chlorine is introduced to said stream in said conduit means at a weight ratio of said molecular chlorine to said removed stream in the range of from about 0.0001:1 to about 0.005:1.

17. The method of claim 15 wherein said stream flowing in said conduit means leaves said conduit means and wherein the temperature of said leaving stream is at least about 20 Celsius degrees less than the temperature of said removed stream.

18. The method of claim 15 wherein said stream flowing in said conduit means leaves said conduit means and wherein the temperature of said leaving stream is at least about 40 Celsius degrees less than the temperature of said removed stream.

19. The method of claim 15 wherein said stream flowing in said conduit means leaves said conduit means and wherein the temperature of said leaving stream is at least about 60 Celsius degrees less than the temperature of said removed stream.

20. The method of claim 1 wherein pyrolysis of 1,2-dichloroethane to produce vinyl chloride is conducted within said conduit means at temperatures in the range of from about 325° C. to about 650° C.

21. The method of claim 15 wherein pyrolysis of 1,2-dichloroethane to produce vinyl chloride is conducted within said conduit means at temperatures in the range of from about 350° C. to about 650° C.

* * * * *